United States Patent
Takagi et al.

(10) Patent No.: US 7,148,047 B2
(45) Date of Patent: Dec. 12, 2006

(54) L-CYSTEINE PRODUCING BACTERIUM AND METHOD FOR PRODUCING L-CYSTEINE

(75) Inventors: Hiroshi Takagi, Fukui (JP); Masaru Wada, Yoshida-gun (JP); Shigeru Nakamori, Yoshida-gun (JP)

(73) Assignee: Ajinomoto Co., Inc., Tokyo (JP)

( * ) Notice: Subject to any disclaimer, the term of this patent is extended or adjusted under 35 U.S.C. 154(b) by 183 days.

(21) Appl. No.: 10/060,218

(22) Filed: Feb. 1, 2002

(65) Prior Publication Data

US 2003/0077766 A1     Apr. 24, 2003

(30) Foreign Application Priority Data

Feb. 9, 2001    (JP)    ............................. 2001-034486

(51) Int. Cl.
  C12N 9/10    (2006.01)
  C12N 1/12    (2006.01)
  C12P 13/12   (2006.01)
  C07K 1/00    (2006.01)
  C07H 21/02   (2006.01)

(52) U.S. Cl. ...................... 435/193; 435/160; 435/113; 435/183; 435/252.1; 530/350; 536/23.1

(58) Field of Classification Search ................. 435/106, 435/113, 183, 193, 252.1; 530/350; 536/23.1
See application file for complete search history.

(56) References Cited

FOREIGN PATENT DOCUMENTS

| CA | 2235752    | * | 5/1997 |
| WO | WO 97/15673 |   | 6/1997 |

OTHER PUBLICATIONS

S. Nakamori, et al., Applied and Environmental Microbiology, vol. 64, No. 5, XP-002115630, pp. 1607-1611, "Overproduction of L-Cysteine and L-Cystine by *Escherichia coli* strains with a genetically Altered Serine Acetyltransferase", May 1998.

R. Kraemer, Journal of Biotechnology, vol. 45, No. 1, XP-004036833, pp. 1-21, "Genetic and Physiological Approaches for the production of Amino Acids", Feb. 12, 1996.

Patent Abstracts of Japan, JP 11-155571, Jun. 15, 1999.

N. M. Kredich, et al., The Journal of Biological Chemistry, vol. 241, No. 21, pp. 4955-4965, "The Enzymic Synthesis of l-cysteine in *Escherichia coli* and *Salmonella typhimurium*", Nov. 10, 1966.

D. Denk, et al., Journal of Gernal Microbiology, vol. 133, pp. 515-525, "L-Cysteine Biosynthesis in *Escherichia coli*: Nucleotide Sequence and Expression of the Serien Acetyltransferase (cysE) Gene from the Wild-Type and a Cysteine-Excreting Mutant", 1987.

I. Rossol, et al., Journal of Bacteriology, vol. 174, No. 9, pp. 2968-2977, "The Corynebacterium Glutamicum aecD Gene Encodes a C-S Lyase with α,β-Elimination Activity that Degrades Aminoethylcysteine", May 1992.

\* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

L-cysteine is produced by culturing a coryneform bacterium in which intracellular serine acetyltransferase activity is increased by transformation with a gene coding for serine acetyltransferase, such modification of an expression control sequence of a gene coding for serine acetyltransferase that expression of the gene in a cell should be enhanced and for forth, preferably in which L-cysteine decomposition system is further suppressed, in a medium to produce and accumulate L-cysteine in culture and collecting the L-cysteine from the culture.

4 Claims, No Drawings

L-CYSTEINE PRODUCING BACTERIUM AND METHOD FOR PRODUCING L-CYSTEINE

BACKGROUND OF THE INVENTION

1. Field of the Invention

The present invention relates to a method for producing L-cysteine, more precisely a novel coryneform bacterium suitable for the production of L-cysteine and a method for producing L-cysteine utilizing the bacterium. L-Cysteine and L-cysteine derivatives are used in the fields of drugs, cosmetics and foods.

2. Description of the Related Art

L-Cysteine is conventionally obtained by extracting it from keratin-containing materials such as hairs, horns and feathers or microbial enzymatic conversion utilizing DL-2-aminothiazoline-4-carboxylic acid as a precursor. Furthermore, it is also attempted to produce L-cysteine by fermentation utilizing a microorganism.

The biosynthesis of L-cysteine have been studied in detail for bacteria such as *Escherichia coli* (Kredich, N. M. et al., *J. Biol. Chem.*, 241, 4955–4965 (1966); Kredich, N. M. et al., 1987, Biosynthesis of Cysteine, In: Neidhardt, F. C., et al. (eds), *Escherichia coli* and *Salmonella typhimurium*: Cellular and Molecular Biology, Vol.1, American Society for Microbiology, Washington D.C., 419–428), and it has been elucidated that L-cysteine is produced from L-serine through reactions of two steps. In *Escherichia coli*, the first reaction is activation of L-serine by acetyl-CoA, and it is catalyzed by serine acetyltransferase (EC 2.3.1.30, also abbreviated as "SAT" hereinafter). The second reaction is a reaction by which L-cysteine is produced from O-acetylserine that is produced by the above reaction, and it is catalyzed by O-acetylserine (thiol) lyase.

Further, it is also known that, in *Escherichia coli*, decomposition of L-cysteine is suppressed by reduction of cysteine desulfhydrase (also abbreviated as "CD" hereinafter) activity (Japanese Patent Laid-open Publication (Kokai) No. 11-155571).

In *Escherichia coli*, genes coding for SAT (cysE) have been cloned from a wild strain and an L-cysteine secreting mutant strain (Denk, D. and Boeck, A., *J. General Microbiol.*, 133, 515–525 (1987)). Further, the nucleotide sequences of these cysE have been determined, and it has been reported that the methionine residue at a position of 256 is replaced with an isoleucine residue in SAT of which feedback inhibition by L-cysteine is decreased. Furthermore, there has also been disclosed a method of producing L-cysteine or the like by using a DNA coding for SAT of which feedback inhibition by L-cysteine is reduced by a mutation different from the aforementioned mutation (International Patent Publication WO97/15673). This SAT has a mutation in the region from the 97th amino acid residue to the 273rd amino acid residue, or a deletion of a C-terminus region from the 227th amino acid residue.

While there were known techniques for producing L-cysteine by utilizing a gene coding for SAT of which feedback inhibition by L-cysteine was reduced as described above, the inventors of the present invention found that productivity of L-cysteine of a bacterium belonging to the genus *Escherichia* containing SAT of which feedback inhibition by L-cysteine was reduced was unstable. And they also found that this instability could be eliminated, i.e., the productivity could be stabilized, by reducing the intracellular CD activity, and they successfully created an *Escherichia coli* strain that stably produced L-cysteine (Japanese Patent Laid-open Publication No. 11-155571).

Further, there has also been disclosed a method for producing L-cysteine and so forth by using a microorganism, specifically *Escherichia coli*, that excessively expresses a gene coding for a protein suitable for discharging antibiotics or other toxic substances from a cell (gene for excretion) (Japanese Patent No. 29920110).

On the other hand, as for *Corynebacterium glutamicum*, the aecD gene has been identified as a gene that imparts S-(β-aminoethyl)-cysteine (AEC) resistance (Rossol, I. et al., *J. Bacteriol.*, 174 (9), 2968–2977 (1992)). It has been demonstrated that the aecD gene is not indispensable for growth, it is involved in the AEC resistance only when it is amplified, and a protein encoded by this gene has C-S lyase activity of which substrate is AEC, cysteine or the like. Rossol et al. paid attention to the fact that lyase could catalyze elimination reaction and reverse synthetic reaction like synthetase, and suggested novel enzymatic synthesis of sulfur-containing amino acids. However, since any example of successful production of sulfur-containing amino acids by fermentation using a microorganism had scarcely been known, they mentioned only an enzymatic synthesis method using the reverse reaction as for possible use of the C-S lyase.

As described above, there are several reports about the breeding of L-cysteine producing bacteria belonging to the genus *Escherichia*, and enzymes involved in the L-cysteine decomposition of *Corynebacterium glutamicum* have also been reported to a certain extent. However, any example of L-cysteine production by fermentation to such an extent that L-cysteine can be collected from a medium has not been known for coryneform bacteria.

SUMMARY OF THE INVENTION

The present invention was accomplished in view of the aforementioned current technical situation. An object is to create a coryneform bacterium having L-cysteine producing ability and thereby provide a method for producing L-cysteine using the bacterium.

The inventors of the present invention assiduously studied in order to achieve the aforementioned object. As a result, they found that L-cysteine producing ability can be imparted to a coryneform bacterium by, for example, increasing intracellular serine acetyltransferase activity. They further found that L-cysteine producing ability can be enhanced by suppressing the L-cysteine decomposition system, and thus accomplished the present invention.

That is, the present invention provides the followings.

(1) A coryneform bacterium having L-cysteine producing ability.

(2) The coryneform bacterium according to (1), which is modified so that intracellular serine acetyltransferase activity should be increased.

(3) The coryneform bacterium according to (2), wherein the intracellular serine acetyltransferase activity is increased by harboring serine acetyltransferase of which feedback inhibition by L-cysteine is reduced.

(4) The coryneform bacterium according to (3), wherein the serine acetyltransferase of which feedback inhibition by L-cysteine is reduced contains a mutation for replacing an amino acid residue corresponding to the methionine residue at a position of 256 of a wild-type serine acetyltransferase with an amino acid residue other than lysine residue and leucine residue, or a mutation for deleting a C-terminal region from an amino acid residue corresponding to the methionine residue at a position of 256 of the wild-type serine acetyltransferase.

(5) The coryneform bacterium according to any one of (2) to (4), wherein the serine acetyltransferase activity is increased by increasing expression amount of a serine acetyltransferase gene.

(6) The coryneform bacterium according to (5), wherein the intracellular serine acetyltransferase activity is increased by transformation with a gene coding for serine acetyltransferase, or such modification of an expression regulatory sequence or a gene involved in expression control of the gene coding for the serine acetyltransferase in a cell of the bacterium that expression of the gene should be enhanced.

(7) The coryneform bacterium according to (5), wherein the gene coding for the serine acetyltransferase is cysE of a bacterium belonging to the genus *Escherichia*.

(8) The coryneform bacterium according to any one of (1) to (6), wherein an L-cysteine decomposition system is further suppressed.

(9) The coryneform bacterium according to (8), wherein the L-cysteine decomposition system is suppressed by such modification that intracellular cysteine desulfhydrase activity should be reduced.

(10) The coryneform bacterium according to (9), wherein the intracellular cysteine desulfhydrases activity is reduced by disrupting aecD gene.

(11) A method for producing L-cysteine, which comprises culturing a coryneform bacterium according to any one of (1) to (10) in a medium to produce and accumulate L-cysteine in culture and collecting the L-cysteine from the culture.

In the present invention, the L-cysteine producing ability means an ability of the bacterium of the present invention to accumulate L-cysteine in a medium in such an amount that the L-cysteine can be collected from the medium when the bacterium is cultured in the medium. An ability to produce L-cysteine to such a degree that is essential for the cell growth does not fall within the scope of the L-cysteine producing ability referred to in the present invention.

Further, the "suppression of L-cysteine decomposition system" means that activity of at least one enzyme involved in the decomposition of cysteine is reduced or eliminated. The "reduction of feedback inhibition" also means a case where the feedback inhibition is substantially cancelled, in addition to a case where the reduced feedback inhibition remains. In the present invention, L-cysteine means reduced type L-cysteine, L-cystine or mixtures thereof unless otherwise indicated.

Since the coryneform bacterium of the present invention has L-cysteine producing ability, it is useful as a material for production of L-cysteine by fermentation and breeding of further L-cysteine producing bacteria.

PREFERRED EMBODIMENTS OF THE INVENTION

Hereafter, the present invention will be explained in detail.

<1> Coryneform bacterium of the present invention

The bacterium of the present invention is a coryneform bacterium having L-cysteine producing ability. In the present invention, "coryneform bacteria" also include those having hitherto been classified into the genus *Brevibacterium*, but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria are mentioned below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes*
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Brevibacterium ammoniagenes*
*Brevibacterium album*
*Brevibacterium cerium*
*Microbacterium ammoniaphilum*

Specifically, the following strains can be exemplified.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, 13032, 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

To obtain these strains, one can be provided them from, for example, the American Type Culture Collection (10801 University Boulevard, Manassas, Va. 20110-2209, United States of America). That is, each strain is assigned its registration number, and one can request provision of each strain by utilizing its registration number. The registration numbers corresponding to the strains are indicated on the catalog of the American Type Culture Collection. Further, the AJ12340 strain was deposited on Oct. 27, 1987 at the National Institute of Bioscience and Human-Technology, Agency of Industrial Science and Technology, Ministry of International Trade and Industry (currently, the Independent Administrative Corporation, National Institute of Advanced Industrial Science and Technology, International Patent Organism Depositary, Chuo Dai-6, 1-1 Higashi 1-Chome, Tsukuba-shi, Ibaraki-ken, Japan, postal code: 305-8566) as an international deposition under the provisions of the Budapest Treaty, and received an accession number of FERM BP-1539. The AJ12418 strain was deposited on Jan.

5, 1989 at the National Institute of Bioscience and Human-Technology, Agency of Industrial Science and Technology, Ministry of International Trade and Industry as an international deposition under the provisions of the Budapest Treaty and received an accession number of FERM BP-2205.

The first embodiment of the bacterium of the present invention is a coryneform bacterium having increased intracellular serine acetyltransferase activity.

The expression of "modified so that intracellular serine acetyltransferase (henceforth also abbreviated as "SAT") activity should be increased" means that the SAT activity per cell has become higher than that of a unmodified strain, for example, a wild-type coryneform bacterium. For example, there can be mentioned a case where number of SAT molecules per cell increases, a case where SAT activity per SAT molecule increases and so forth. Further, as a wild-type coryneform bacterium that serves as an object for comparison, for example, the *Corynebacterium glutamicum* ATCC 13032 can be mentioned. It is considered that, as a result of enhancement of intracellular SAT activity, the production amount of L-cysteine in coryneform bacteria is increased.

Enhancement of SAT activity in a coryneform bacterium cell can be attained by increasing copy number of a gene coding for SAT. For example, a recombinant DNA can be prepared by ligating a gene fragment coding for SAT with a vector functioning in the bacterium, preferably a multi-copy type vector, and introduced into a host coryneform bacterium to transform it.

As the SAT gene, any of genes derived from coryneform bacteria and genes derived from other organisms such as bacteria belonging to the genus *Escherichia* can be used. The SAT gene may be, in addition to a wild-type SAT gene, one coding for a protein having an amino acid sequence including such substitution, deletion, insertion, addition or inversion of one or several amino acid residues that the activity for catalyzing the activation of L-serine with acetyl-CoA should not be substantially degraded.

As the gene coding for SAT of *Escherichia coli*, cysE has been cloned from a wild strain and an L-cysteine secreting mutant strain (Denk, D. and Boeck, A., *J. General Microbiol.*, 133, 515–525 (1987); cysE gene shown as SEQ ID NO: 7 and the encoded serine acetyltransferase appears as SEQ ID NO: 8). Therefore, a SAT gene can be obtained by PCR (polymerase chain reaction; refer to White, T.J. et al., *Trends Genet.*, 5, 185 (1989)) utilizing primers prepared based on the nucleotide sequences and chromosomal DNA of coryneform bacterium as a template (refer to Japanese Patent Laid-open Publication No. 11-155571). Genes coding for SAT of other microorganisms can also be obtained in a similar manner.

The chromosomal DNA can be prepared from a bacterium, which is a DNA donor, by the method of Saito and Miura (refer to H. Saito and K. Miura, *Biochem. Biophys. Acta*, 72, 619 (1963), Text for Bioengineering Experiments, Edited by the Society for Bioscience and Bioengineering, Japan, pp.97–98, Baifukan, 1992), for example.

If the SAT gene amplified by the PCR method is ligated to a vector DNA autonomously replicable in a cell of *Escherichia coli* and/or coryneform bacteria to prepare a recombinant DNA and this is introduced into *Escherichia coli*, subsequent procedures become easy. Examples of the vector autonomously replicable in a cell of *Escherichia coli* include pUC19, pUC18, pHSG299, pHSG399, pHSG398, RSF1010, pBR322, pACYC184, pMW219 and so forth.

A vector that functions in coryneform bacteria means, for example, a plasmid that can autonomously replicate in coryneform bacteria. Specific examples thereof include the followings.
pAM330 (refer to Japanese Patent Laid-open Publication No. 58-67699)
pHM1519 (refer to Japanese Patent Laid-open Publication No. 58-77895)
pSFK6 (refer to Japanese Patent Laid-open Publication No. 2000-262288)

Moreover, if a DNA fragment having an ability to make a plasmid autonomously replicable in coryneform bacteria is taken out from these vectors and inserted into the aforementioned vectors for *Escherichia coli*, they can be used as a so-called shuttle vector autonomously replicable in both of *Escherichia coli* and coryneform bacteria.

Examples of such a shuttle vector include those mentioned below. There are also indicated microorganisms that harbor each vector, and accession numbers thereof at the international depositories are shown in the parentheses, respectively.

pAJ655 *Escherichia coli* AJ11882 (FERM BP-136)
    *Corynebacterium glutamicum* SR8201 (ATCC 39135)
pAJ1844 *Escherichia coli* AJ11883 (FERM BP-137)
    *Corynebacterium glutamicum* SR8202 (ATCC 39136)
pAJ611 *Escherichia coli* AJ11884 (FERM BP-138)
pAJ3148 *Corynebacterium glutamicum* SR8203 (ATCC 39137)
pAJ440 *Bacillus subtilis* AJ11901 (FERM BP-140)
pHC4 *Escherichia coli* AJ12617 (FERM BP-3532)

Further, the plasmid pVK7 described in the examples (refer to Japanese Patent Laid-open Publication No. 11-266881) is also suitable as a shuttle vector of *Escherichia coli* and coryneform bacteria.

These vectors can be obtained from the deposited microorganisms as follows. That is, microbial cells collected in their exponential growth phase are lysed by using lysozyme and SDS, and centrifuged at 30000×g. The supernatant obtained from the lysate is added with polyethylene glycol, fractionated and purified by cesium chloride-ethidium bromide equilibrium density gradient centrifugation.

In order to prepare a recombinant DNA by ligating a SAT gene and a vector that can function in a cell of coryneform bacterium, a vector is digested with a restriction enzyme corresponding to the terminus of the SAT gene. Ligation is usually performed by using a ligase such as T4 DNA ligase.

To introduce the recombinant DNA prepared as described above into a microorganism, any known transformation methods that have hitherto been reported can be employed. For instance, employable are a method of treating recipient cells with calcium chloride so as to increase the permeability of the cells for DNA, which has been reported for *Escherichia coli* K-12 (Mandel, M. and Higa, A., *J. Mol. Biol.*, 53, 159 (1970)), and a method of preparing competent cells from cells which are at the growth phase followed by introducing the DNA thereinto, which has been reported for *Bacillus subtilis* (Duncan, C. H., Wilson, G. A. and Young, F. E., *Gene*, 1, 153 (1977)). In addition to these, also employable is a method of making DNA-recipient cells into protoplasts or spheroplasts, which can easily take up recombinant DNA, followed by introducing the recombinant DNA into the DNA-acceptor cells, which is known to be applicable to *Bacillus subtilis*, actinomycetes and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Sci. USA*, 75, 1929 (1978)). The transformation of coryneform bacteria can also be performed by the electroporation method (Sugimoto et al., Japanese Patent Laid-open No. 2-207791).

Increase of copy number of SAT gene can also be achieved by introducing multiple copies of the SAT gene into chromosomal DNA of coryneform bacteria. In order to introduce multiple copies of the SAT gene into chromosomal DNA of coryneform bacteria, homologous recombination is carried out for sequences whose multiple copies exist in the chromosomal DNA as targets. As sequences whose multiple copies exist in the chromosomal DNA, repetitive DNA, inverted repeats existing at the end of a transposable element can be used. Also, as disclosed in Japanese Patent Laid-open No. 2-109985, it is possible to incorporate the SAT gene into transposons, and allow them to be transferred to introduce multiple copies of the gene into the chromosomal DNA.

Enhancement of the SAT activity can also be attained by, besides being based on the aforementioned gene amplification, replacing an expression control sequence such as a promoter for the SAT gene on chromosomal DNA or plasmid, with a stronger one (refer to Japanese Patent Laid-open Publication No. 1-215280). For example, lac promoter, trp promoter, trc promoter and so forth are known as strong promoters. The substitution of expression control sequence can also be performed by, for example, gene substitution using a temperature sensitive plasmid. Examples of the temperature sensitive plasmid for coryneform bacteria include p48K, pSFKT1, pSFKT2, pSFKT3, pSFKT4, pSFKT5 and pSFKT6 (refer to Japanese Patent Laid-open Publication No. 2000-262288 for these), pHSC4 (refer to France Patent Laid-open Publication No. 2667875, 1992 and Japanese Patent Laid-open Publication No. 5-7491) and so forth. Furthermore, it is also possible to introduce nucleotide substitution for several nucleotides in the promoter region of the SAT gene to modify the promoter into a stronger one as disclosed in International Patent Publication WO00/18935. The expression of the SAT gene is enhanced by such substitution or modification of the promoter and thus the SAT activity is enhanced. These modifications of expression control sequence may be combined with increase of copy number of the SAT gene.

Furthermore, when a suppression mechanism exists for the expression of the SAT gene, expression of the SAT gene can also be enhanced by modifying an expression control sequence or a gene involved in the suppression so that the suppression should be eliminated or reduced.

The intracellular SAT activity of coryneform bacteria can also increased by making a coryneform bacterium contain SAT of which feedback inhibition by L-cysteine is reduced (henceforth also referred to as "mutant SAT"). Examples of the mutant SAT include SAT having a mutation for replacing an amino acid residue corresponding to the methionine residue at a position of a wild-type SAT with an amino acid residue other than lysine residue and leucine residue, or a mutation for deleting a C-terminal region from an amino acid residue corresponding to the methionine residue at a position of the wild-type SAT. Examples of the amino acid residue other than lysine residue and leucine residue include the 17 kinds of amino acid residues among the amino acids constituting ordinary proteins except for methionine residue, lysine residue and leucine residue. More specifically, isoleucine residue can be mentioned.

The mutant SAT used in the present invention may be one having an amino acid sequence including such substitution, deletion, insertion, addition or inversion of one or several amino acid residues that the activity for catalyzing the activation of L-serine with acetyl-CoA should not be substantially degraded, in addition to the aforementioned mutation that reduces feedback inhibition by L-cysteine. In SAT having such a mutation, the position of the methionine residue at a position of 256 may be changed. Even in such a case, a mutant SAT of which feedback inhibition by L-cysteine is reduced can be obtained by replacing an amino acid residue corresponding to the methionine residue at a position of 256 with an amino acid residue other than lysine residue and leucine residue.

A coryneform bacterium can be made to contain a mutant SAT by introducing such a mutation that the feedback inhibition of the encoded SAT by L-cysteine should be eliminated into the intracellular SAT gene. Such a mutation can be introduced by a treatment by ultraviolet irradiation or with a mutagenizing agent used for usual mutagenesis treatment such as N-methyl-N'-nitro-N-nitrosoguanidine (NTG) or a nitrous acid.

A coryneform bacterium can also be made to contain a mutant SAT by introducing a mutant SAT gene into the coryneform bacterium. The mutant SAT gene can be obtained by introducing such a mutation that the feedback inhibition of the encoded SAT by L-cysteine should be eliminated, for example, a mutation for replacing an amino acid residue corresponding to the methionine residue at a position of 256 of a wild-type SAT with an amino acid residue other than lysine residue and leucine residue, or a mutation for deleting a C-terminal region from an amino acid residue corresponding to the methionine residue at a position of 256 of the wild-type SAT into the wild-type SAT gene. As the method of introducing a desired mutation into a wild-type SAT gene, site-specific mutagenesis can be mentioned. As a mutant SAT gene, mutant cysE coding for a mutant SAT of *Escherichia coli* is known (refer to International Patent Publication WO97/15673 and Japanese Patent Laid-open Publication No. 11-155571).

The second embodiment of the bacterium of the present invention is a coryneform bacterium in which intracellular SAT activity is increased and the L-cysteine decomposition system is suppressed. In *Escherichia coli*, CD and cystathione β-lyase are known as enzymes involved in decomposition of L-cysteine. Hereafter, methods for reducing or eliminating CD activity of coryneform bacteria will be exemplified.

To reduce or eliminate the intracellular CD activity of coryneform bacteria, there can be used, for example, a method of treating the coryneform bacteria by ultraviolet irradiation or with a mutagenizing agent used for usual mutagenesis treatment such as N-methyl-N'-nitro-N-nitrosoguanidine (NTG) or a nitrous acid and selecting a mutant strain in which the CD activity is reduced. Coryneform bacteria having reduced CD activity can also be obtained by gene disruption, besides the mutagenesis treatment. That is, a coryneform bacterium can be transformed with a DNA containing a aecd gene modified with deletion of internal sequence of the gene coding for CD so as not to produce CD functioning normally (deletion type CD gene), so that recombination between the deletion type CD gene and the CD gene on the chromosome should occur, to disrupt the CD gene on the chromosome. Such gene disruption by gene substitution utilizing homologous recombination has already been established, and there are methods utilizing a linear DNA, a plasmid that contains a temperature sensitive replication origin and so forth.

A CD gene on host chromosome can be replaced with the deletion type CD gene, for example, as follows. That is, a recombinant DNA is prepared by inserting a temperature sensitive replication origin, a mutant CD gene and a marker gene for resistance to a drug such as chloramphenicol, and a coryneform bacterium is transformed with the recombinant DNA. Further, the resultant transformant strain is cultured at a temperature at which the temperature sensitive replication origin does not function, and then the transformant strain can be cultured in a medium containing the drug to obtain a transformant strain in which the recombinant DNA is incorporated into the chromosomal DNA.

In such a strain in which recombinant DNA is incorporated into chromosomal DNA as described above, the mutant CD gene is recombined with the CD gene originally present on the chromosome, and the two fusion genes of the chromosomal CD gene and the deletion type CD gene are inserted into the chromosome so that the other portions of the recombinant DNA (vector segment, temperature sensitive replication origin and drug resistance marker) should be present between the two fusion genes. Therefore, the transformant strain expresses normal CD, because the normal CD gene is dominant in this state.

Then, in order to leave only the deletion type CD gene on the chromosomal DNA, one copy of the CD gene is eliminated together with the vector segment (including the temperature sensitive replication origin and the drug resistance marker) from the chromosomal DNA by recombination of two of the CD genes. In this case, the normal CD gene is left on the chromosomal DNA and the deletion type CD gene is excised from the chromosomal DNA, or to the contrary, the deletion type CD gene is left on the chromosomal DNA and the normal CD gene is excised from the chromosome DNA. In the both cases, the excised DNA may be harbored in the cell as a plasmid when the cell is cultured at a temperature at which the temperature sensitive replication origin can function. Subsequently, if the cell is cultured at a temperature at which the temperature sensitive replication origin cannot function, the CD gene on the plasmid is eliminated together with the plasmid from the cell. Then, a strain in which CD gene is disrupted can be obtained by selecting a strain in which the deletion type CD gene is left on the chromosome using PCR, Southern hybridization or the like.

As described in the examples mentioned later, it was clarified that major CD was encoded by the aecD gene in *Brevibacterium flavum* and *Corynebacterium glutamicum* by purification and amino acid sequence determination of proteins having the CD activity and cloning and sequencing of genes coding for such proteins.

Reduction or elimination of the CD activity in a gene-disrupted strain or mutant strain can be confirmed by measuring the CD activity of cell extract of a candidate strain by the method of Kredich et al. (*J. Biol. Chem.,* 248, 6187–6196 (1973)) and comparing it with the CD activity of a parent strain.

In a similar manner, activities of other enzymes involved in decomposition of L-cysteine can be reduced or eliminated.

An aecD-disrupted strain of *Corynebacterium glutamicum*, IR33, has already been constructed and reported (I. Rossol & A. Puhler, *J. Bacterial.,* 174, 2968–2977 (1992)).

<2> Method for Producing L-cysteine

L-cysteine can be produced by culturing a coryneform bacterium having L-cysteine producing ability and intracellular SAT activity increased as described above, or such a coryneform bacterium in which the L-cysteine decomposition system is further suppressed in a medium to produce and accumulate L-cysteine in the medium and correcting the L-cysteine from the medium.

Although L-cysteine produced by the method of the present invention may contain cystine in addition to reduced type cysteine, the object of the production method of the present invention include cysteine and mixture of reduced type cysteine and cystine.

In order to produce L-cysteine by using the coryneform bacterium of the present invention, culture can be performed in a conventional manner using a usual medium containing a carbon source, nitrogen source and mineral salts as well as organic trace nutrients such as amino acids and vitamins, as required. Either a synthetic medium or a natural medium may be used. Any kinds of carbon source and nitrogen source may be used so long as they can be utilized by a strain to be cultured.

As the carbon source, there are used sugars such as glucose, glycerol, fructose, sucrose, maltose, mannose, galactose, starch hydrolysate and molasses, and organic acids such as acetic acid and citric acid, and alcohols such as ethanol can also be used each alone or in a combination with other carbon sources.

As the nitrogen source, there are used ammonia, ammonium salts such as ammonium sulfate, ammonium carbonate, ammonium chloride, ammonium phosphate and ammonium acetate, nitrate salts and so forth.

As the organic trace nutrients, amino acids, vitamins, fatty acids, nucleic acids, those containing these substances such as peptone, casamino acid, yeast extract and soybean protein decomposition product and so forth are used. When an auxotrophic mutant that requires an amino acid or the like for its growth is used, it is preferable to supplement the required nutrient.

As the mineral salts, phosphates, magnesium salts, calcium salts, iron salts, manganese salts and so forth are used.

The culture is performed as aeration culture, while the fermentation temperature is controlled to be 20–45° C., and pH to be 5–9. When pH falls during the culture, the medium is neutralized by addition of calcium carbonate or with an alkali such as ammonia gas. A substantial amount of L-cysteine is accumulated in the culture broth after 10 hours to 120 hours of culture in such a manner as described above.

Collection of L-cysteine from the culture broth may be performed by a combination of conventional methods, for example, usual methods utilizing ion exchange resins, precipitation and so forth.

BEST MODE FOR CARRYING OUT THE INVENTION

Hereafter, the present invention will be explained more specifically with reference to the following examples.

<1> Identification of L-cysteine Decomposition Enzyme in Coryneform Bacteria

For the purpose of identifying L-cysteine decomposition enzyme in coryneform bacteria, an enzyme showing the CD activity was purified from a disrupted cell suspension of *Brevibacterium flavum* 2247 strain (ATCC 14067) by various chromatographic techniques. For the measurement of the enzyme activity, the method of Kredich et al. (*J. Biol. Chem.,* 248, 6187–6196 (1973)) was used. The ATCC 14067 strain was cultured in a minimal medium (5 g/L of glucose, 1.5 g/L of urea, 1.5 g/L of ammonium sulfate, 1 g/L of $KH_2PO_4$, 3 g/L of $K_2HPO_4$, 0.1 g/L of $MgSO_4 \cdot 7H_2O$, 1 mg/L of $CaCl_2$, 30 μg/L of biotin, 100 μg/L of thiamine, 10 mg/L of $FeSO_4 \cdot 7H_2O$ and 10 mg/L of $MnSO_4 \cdot 4H_2O$, pH 7.0) and then disrupted cell suspension was prepared. From the disrupted cell suspension, a fraction showing the CD activity was successively purified by using DEAE-Sepharose FF (Amercham Pharmacia Biotech), BUTYL-Toyopearl 650M (Tohso), MonoQ (Amercham Pharmacia Biotech), RESOURCE IOS (Amercham Pharmacia Biotech) and Superdex-200 (Amercham Pharmacia Biotech) to obtain a protein solution showing substantially single band in SDS-PAGE. The obtained enzyme protein showed a molecular weight of about 43 kDa in SDS-PAGE under a reduced condition.

The N-terminal amino acid sequence of the protein having the CD activity, which was purified as described above, and the amino acid sequence of one of peptides obtained by digesting the protein with lysyl endopeptidase were determined by the Edman degradation method. The results are shown below.

(N-terminus amino acid sequence) p0 MRFPELEELKNR-RTLKWTRFPEDVL (SEQ ID NO: 1)

(Internal amino acid sequence)
ILREEGK (SEQ ID NO: 2)

When a protein having the amino acid sequence of the above internal sequence was searched by using FASTA, it showed 100% of coincidence with a part of a product of the aecD gene derived from *Corynebacterium glutamicum* (I. Rossol & A. Puhler, *J. Bacteriol.*, 174, 2968–2977 (1992): aecD gene shown as SEQ ID NO: 9 and the encoded cysteine desulfhydrase appears as SEQ ID NO: 10).

Primers 1 and 2 having the following nucleotide sequences were prepared based on a DNA sequence deduced from the aforementioned N-terminus amino acid sequence and the internal amino acid sequence, and PCR was performed by using chromosomal DNA of the ATCC 14067 strain as a template.

```
(Primer 1)
AARTGGACNMGNTTYCCNGA        (SEQ ID NO: 3)

(Primer 2)
CTTACCCTCCTCACGAAGAA        (SEQ ID NO: 4)
```

As a result of nucleotide sequencing of the obtained fragment, it was found that it substantially coincided with the reported nucleotide sequence of the aecD gene of the *Corynebacterium glutamicum*. However, the N-terminal amino acid sequence of the protein determined as described above coincided with a sequence located from a position upstream from the initiation codon of the previously reported aecD gene by 129 bp. Based on these results, it was determined that the purified protein having the CD activity was an aecD gene product and the initiation codon ATG of the aecD gene correctly located at a position upstream from the initiation codon of the previously reported aecD gene by 129 bp at least in the ATCC 14067 strain.

The nucleotide sequence of the aecD gene of *Corynebacterium glutamicum* obtained as described above and the amino acid sequence encoded by the nucleotide sequence are shown as SEQ ID NOS: 5 and 6.

<2> Measurement of CD Activity in aecD-disrupted Strain of *Corynebacterium glutamicum*

An aecD disrupted-strain IR33 of *Corynebacterium glutamicum* had been already constructed and reported (I. Rossol & A. Puhler, *J. Bacteriol.*, 174, 2968–2977 (1992)). The IR33 strain was a strain in which the aecD gene on chromosome was disrupted by homologous recombination using a plasmid pIR33 containing aecD gene inactivated by insertion of a chloramphenicol resistance gene cassette. The CD activity of the IR33 strain described in the above reference and its parent strain, the ATCC 13032 strain, was measured. After cell disruption suspensions were prepared, the CD activity was measured by the method of Kredich et al. The results are shown in Table 1. The CD activity of IR33 strain was reduced to a level of about ⅓ of the activity of the wild strain, ATCC 13032 strain.

TABLE 1

| Strain | CD activity (mU/mg) |
|---|---|
| ATCC13032 | 38 |
| IR33 | 12 |

As described above, the CD activity was markedly reduced by the disruption of the aecD gene, and thus it was confirmed that the major CD activity was encoded by the aecD gene in *Corynebacterium glutamicum*.

<3> Introduction of Plasmid Containing Desensitized Type SAT Gene Derived From *Escherichia coil* into aecD-disrupted strain A wild-type SAT gene (cysE) derived from *Escherichia coil* or a gene coding for desensitized type SAT which had been desensitized by mutating the Met residue at a position of 256 of the wild-type SAT gene into an Ile residue (Japanese Patent Laid-open Publication No. 11-155571) was introduced into the aecD-disrupted strain of *Corynebacterium glutamicum*, IR33, and the wild-strain, ATCC 13032.

A fragment containing SAT gene was excised by digestion with EcoRI from each of the plasmid pCE containing the wild-type SAT gene and the plasmid pCEM256I containing the desensitized type SAT gene (Japanese Patent Laid-open Publication No. 11-155571), and inserted into the EcoRI site of the plasmid pVK7, which was a shuttle vector between coryneform bacteria and *Escherichia coil* (refer to Japanese Patent Laid-open Publication No. 11-266881). pVK7 was a plasmid constructed by ligating pAM330 that was a cryptic plasmid of *Brevibacterium lactofermentum* to pHSG299 that was a vector for *Escherichia coli* (Km$^r$, refer to Takeshita, S. et al., *Gene*, 61, 63–74, (1987), Japanese Patent Laid-open Publication No. 10-215883), and contained a multiple cloning site and lacZ' derived from pHSG299.

As described above, there were obtained plasmids inserted with the wild-type SAT gene or the desensitized type SAT gene at lacZ' on pVK7 in the forward direction. The plasmid containing the wild-type SAT gene and the plasmid containing the desensitized type SAT gene were designated as pVK7-CE and pVK7-256, respectively.

Each of pVK7, pVK7-CE and pVK7-256 was introduced into ATCC 13032 and IR33 by electroporation. Transformant strains were selected by using kanamycin resistance as a marker.

<4> Production of L-cysteine and L-cystine

Each of the obtained transformants was plated on an M-CM2G (10 g/L of polypeptone, 10 g/L of yeast extract, 5 g/L of NaCl, 5 g/L of glucose, 0.2 g/L of DL-methionine, pH 7.2) plate containing 25 mg/L of kanamycin, cultured at 31.5° C. for 48 hours, then inoculated into 20 ml of a cysteine production medium having the following composition in a flask, and cultured at 31.5° C. for 72 hours with shaking.

| (cysteine production medium) | |
|---|---|
| Glucose | 100 g/L |
| (NH$_4$)$_2$SO$_4$ | 45 g/L |
| KH$_2$PO$_4$ | 1 g/L |
| MgSO$_4$.7H$_2$O | 1 g/L |
| FeSO$_4$.7H$_2$O | 10 mg/L |
| MnSO$_4$.5H$_2$O | 10 mg/L |
| Thiamin · HCl | 300 mg/L |
| Biotin | 100 µg/L |
| Soybean protein hydrochloric acid hydrolysate "Ajieki" (registered trademark, Ajinomoto Co., Inc.) | 480 µg/L |
| L-Isoleucine | 100 mg/L |
| L-Leucine | 100 mg/L |
| L-Glycine | 100 mg/L |
| DL-Methionine | 100 mg/L |
| CaCO$_3$ | 50 g/L |

Accumulated amount of L-cysteine was measured as the total amount of reduced-type cysteine (L-Cys) and cystine (L-CysH) for a culture broth diluted with 0.5 N HCl in order to dissolve precipitated L-cystine by a bioassay using *Leuconostoc mesenteroides* (Tsunoda T. et al., *Amino acids*, 3, 7–13 (1961)).

TABLE 2

| Host strain | Introduced plasmid | L-Cys + L-CysH accumulation (mg/L) |
|---|---|---|
| ATCC 13032 | pVK7 | <50 |
| ATCC 13032 | pVK7-CE | <50 |
| ATCC 13032 | pVK7-256 | 140 |
| IR33 | pVK7 | <50 |
| IR33 | pVK7-CE | 70 |
| IR33 | pVK7-256 | 250 |

As described above, it was demonstrated that L-cysteine accumulation was caused by amplification of SAT gene derived from *Escherichia coli* in *Corynebacterium glutamicum*. As the SAT gene, the desensitized-type one was more preferred than the wild-type one. Further, L-cysteine accumulation was enhanced by disruption of the aecD gene.

What is claimed is:

1. A recombinant coryneform bacterium having L-cysteine producing ability, wherein said coryneform bacterium has been modified to increase the copy number of a polynucleotide coding for seine acetyltransferase so that the intracellular serine acetyltransferase activity is enhanced as compared to an unmodified coryneform bacterium, or a promoter sequence of the said polynucleotide is modified so that expression of the said polynucleotide is enhanced, whereby the intracellular serine acetyltransferase activity is enhanced as compared to an unmodified coryneform bacterium, wherein said polynucleotide is obtained from a bacterium belonging to the genus Escherichia, wherein the serine acetyltransferase of which feedback inhibition by L-cysteine is reduced, contains a mutation replacing the methionine residue at position 256 of the wild-type serine acetyltransferase with an amino acid residue other than a lysine residue or a leucine residue, or a mutation deleting the C-terminal region beginning from the methionine residue at position 256 of the wild-type serine acetyltransferase;

and wherein said wild-type serine acetyltransferase has the amino acid sequence of SEQ ID NO: 8.

2. The recombinant coryneform bacterium according to claim 1, further comprising modification such that activity of the cysteine desuithydrase of said recombinant coryneform bacterium is reduced as compared to an unmodified coryneform bacterium, wherein said cysteine desulfhydrase has the amino acid sequence of SEQ IID NO: 10.

3. The recombinant coryneform bacterium according to claim 2, wherein the activity of the cysteine desulfhydrase of said recombinant coryneform bacterium is reduced by disrupting a polynucleotide encoding the cysteine desuithydrase, wherein said cysteine desullhydrase has the amino acid sequence of SEQ ID NO: 10.

4. A method for producing L-cysteine, comprising culturing the recombinant coryneform bacterium according to claim 1 in a medium to produce and accumulate L-cysteine in culture and collecting the L-cysteine from the culture.

* * * * *

UNITED STATES PATENT AND TRADEMARK OFFICE
CERTIFICATE OF CORRECTION

PATENT NO. : 7,148,047 B2
APPLICATION NO. : 10/060218
DATED : December 12, 2006
INVENTOR(S) : Hiroshi Takagi et al.

It is certified that error appears in the above-identified patent and that said Letters Patent is hereby corrected as shown below:

Column 21, line 9, " the cysteine desuithydrase of said recombinant "
    should read -- the cysteine desulfhydrase of said recombinant --;
line 12, " amino acid sequence of SEQ 1ID NO: 10. "
    should read -- amino acid sequence of SEQ ID NO: 10. --.

Column 22, lines 4 and 5,
    " the cysteine desuithydrase, wherein said cysteine desullhydrase has the amino "
should read
    -- the cysteine desulfhydrase, wherein said cysteine desulfhydrase has the amino --.

Signed and Sealed this

Twenty-sixth Day of June, 2007

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 25
<212> TYPE: PRT
<213> ORGANISM: Corynebacterium flavum

<400> SEQUENCE: 1

Met Arg Phe Pro Glu Leu Glu Glu Leu Lys Asn Arg Arg Thr Leu Lys
1               5                   10                  15

Trp Thr Arg Phe Pro Glu Asp Val Leu
            20                  25

<210> SEQ ID NO 2
<211> LENGTH: 7
<212> TYPE: PRT
<213> ORGANISM: Corynebacterium flavum

<400> SEQUENCE: 2

Ile Leu Arg Glu Glu Gly Lys
1               5

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (9)..(9)
<223> OTHER INFORMATION: n=a or g to c or t
<220> FEATURE:
<221> NAME/KEY: misc_feature
<222> LOCATION: (12)..(12)
```

```
<223> OTHER INFORMATION: n=a or g to c or t
<220> FEATURE:
<221> NAME/KEY: misc_feature
<222> LOCATION: (18)..(18)
<223> OTHER INFORMATION: n=a or g to c or t

<400> SEQUENCE: 3
aartggacnm gnttyccnga                                                    20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
cttaccctcc tcacgaagaa                                                    20

<210> SEQ ID NO 5
<211> LENGTH: 1620
<212> TYPE: DNA
<213> ORGANISM: Corynebacterium glutamicum
<220> FEATURE:
<221> NAME/KEY: CDS
<222> LOCATION: (232)..(1338)
<223> OTHER INFORMATION:

<400> SEQUENCE: 5
gatatcgccg cttgggactg tgattgggct tacctctttg gcttcgaaca ccggggttga        60
ggtagtggtt acttccatgg tttcctcagc ggaaacggct tggctatcag cactttcacc      120
cgaacagcct gcaagaagtg cgacggctaa cagggctggg attgtcctca acttcacttc      180
gggctccttc ttagtaatag gttcgtagaa aagtttacta agcctgagag t atg cga       237
                                                         Met Arg
                                                           1 ttt cct gaa ctc gaa gaa ttg aag aat cgc cgg acc ttg aaa tgg acc        285
Phe Pro Glu Leu Glu Glu Leu Lys Asn Arg Arg Thr Leu Lys Trp Thr
          5                  10                  15 cgg ttt cca gaa gac gtg ctt cct ttg tgg gtt gcg gaa agt gat ttt        333
Arg Phe Pro Glu Asp Val Leu Pro Leu Trp Val Ala Glu Ser Asp Phe
 20                  25                  30 ggc acc tgc ccg cag ttg aag gaa gct atg gca gat gcc gtt gag cgc        381
Gly Thr Cys Pro Gln Leu Lys Glu Ala Met Ala Asp Ala Val Glu Arg
 35                  40                  45                  50 gag gtc ttc gga tac cca cca gat gct act ggg ttg aat gat gcg ttg        429
Glu Val Phe Gly Tyr Pro Pro Asp Ala Thr Gly Leu Asn Asp Ala Leu
                 55                  60                  65 act gga ttc tac gag cgt cgc tat ggg ttt ggc cca aat ccg gaa agt        477
Thr Gly Phe Tyr Glu Arg Arg Tyr Gly Phe Gly Pro Asn Pro Glu Ser
             70                  75                  80 gtt ttc gcc att ccg gat gtg gtt cgt ggc ctg aag ctt gcc att gag        525
Val Phe Ala Ile Pro Asp Val Val Arg Gly Leu Lys Leu Ala Ile Glu
         85                  90                  95 cat ttc act aag cct ggt tcg gcg atc att gtg ccg ttg cct gca tac        573
His Phe Thr Lys Pro Gly Ser Ala Ile Ile Val Pro Leu Pro Ala Tyr
    100                 105                 110 cct cct ttc att gag ttg cct aag gtg act ggt cgt cag gcg atc tac        621
Pro Pro Phe Ile Glu Leu Pro Lys Val Thr Gly Arg Gln Ala Ile Tyr
115                 120                 125                 130 att gat gcg cat gag tac gat ttg aag gaa att gag aag gcc ttc gct        669
Ile Asp Ala His Glu Tyr Asp Leu Lys Glu Ile Glu Lys Ala Phe Ala
                135                 140                 145
```

```
gac ggt gcg gga tca ctg ttg ttc tgc aat cca cac aac cca ctg ggc    717
Asp Gly Ala Gly Ser Leu Leu Phe Cys Asn Pro His Asn Pro Leu Gly
        150                 155                 160 acg gtc ttt tct gaa gag tac atc cgc gag ctc acc gat att gcg gcg    765
Thr Val Phe Ser Glu Glu Tyr Ile Arg Glu Leu Thr Asp Ile Ala Ala
        165                 170                 175 aag tac gat gcc cgc atc atc gct gat gag atc cac gcg cca ctg gtt    813
Lys Tyr Asp Ala Arg Ile Ile Ala Asp Glu Ile His Ala Pro Leu Val
        180                 185                 190 tat gaa ggc acc cat gtg gtt gct gct ggt gtt tct gag aac gct gca    861
Tyr Glu Gly Thr His Val Val Ala Ala Gly Val Ser Glu Asn Ala Ala
195                 200                 205                 210 aac act tgc atc acc atc acc gca act tct aag gcg tgg aac act gct    909
Asn Thr Cys Ile Thr Ile Thr Ala Thr Ser Lys Ala Trp Asn Thr Ala
                215                 220                 225 ggt ttg aag tgt gct cag atc ttc ttc agt ggt gaa gcc gat gtg aag    957
Gly Leu Lys Cys Ala Gln Ile Phe Phe Ser Gly Glu Ala Asp Val Lys
            230                 235                 240 gcc tgg aag aat ttg tcg gat att acc cgt gac ggt gtg tcc atc ctt   1005
Ala Trp Lys Asn Leu Ser Asp Ile Thr Arg Asp Gly Val Ser Ile Leu
        245                 250                 255 gga ttg atc gct gcg gag aca gtg tac aac gag ggc gaa gaa ttc ctt   1053
Gly Leu Ile Ala Ala Glu Thr Val Tyr Asn Glu Gly Glu Glu Phe Leu
    260                 265                 270 gat gag tca att cag att ctc aag gac aac cgt gac ttt gcg gct gct   1101
Asp Glu Ser Ile Gln Ile Leu Lys Asp Asn Arg Asp Phe Ala Ala Ala
275                 280                 285                 290 gaa ctg gaa aag ctt ggc gtg aag gtc tac gca ccg gac tcc act tat   1149
Glu Leu Glu Lys Leu Gly Val Lys Val Tyr Ala Pro Asp Ser Thr Tyr
                295                 300                 305 ttg atg tgg ttg gac ttc gct ggc acc aag atc gaa gag gcg cct tct   1197
Leu Met Trp Leu Asp Phe Ala Gly Thr Lys Ile Glu Glu Ala Pro Ser
            310                 315                 320 aaa att ctt cgt gag gag ggt aag gtc atg ctg aat gat ggc gca gct   1245
Lys Ile Leu Arg Glu Glu Gly Lys Val Met Leu Asn Asp Gly Ala Ala
        325                 330                 335 ttt ggt ggt ttc acc acc tgc gct cgt ctt aat ttt gcg tgt tcc aga   1293
Phe Gly Gly Phe Thr Thr Cys Ala Arg Leu Asn Phe Ala Cys Ser Arg
    340                 345                 350 gag acc ctt gag gag ggc tgc gcc gta tcg cca gcg tgt tgt aaa       1338
Glu Thr Leu Glu Glu Gly Cys Ala Val Ser Pro Ala Cys Cys Lys
355                 360                 365 taatgagtaa aaagtctgtc ctgattactt ctttgatgct gttttccatg ttcttcggag   1398
ctggaaacct catcttcccg ccgatgcttg gattgtcggc aggaaccaac tatctaccag   1458
ctatcttagg atttctagca acgagtgttc tgctcccggt gctggcgatt atcgcggtgg   1518
tgttgtcggg agaaaatgtc aaggacatgg cttctcgtgg cggtaagatc tttggcctgg   1578
tgtttcctat tgctgcctat ttgtctatcg gcgcgtttta cg                      1620

<210> SEQ ID NO 6
<211> LENGTH: 369
<212> TYPE: PRT
<213> ORGANISM: Corynebacterium glutamicum

<400> SEQUENCE: 6

Met Arg Phe Pro Glu Leu Glu Glu Leu Lys Asn Arg Arg Thr Leu Lys
1               5                   10                  15

Trp Thr Arg Phe Pro Glu Asp Val Leu Pro Leu Trp Val Ala Glu Ser
```

-continued

```
                 20                  25                  30
Asp Phe Gly Thr Cys Pro Gln Leu Lys Glu Ala Met Ala Asp Ala Val
             35                  40                  45

Glu Arg Glu Val Phe Gly Tyr Pro Pro Asp Ala Thr Gly Leu Asn Asp
 50                  55                  60

Ala Leu Thr Gly Phe Tyr Glu Arg Arg Tyr Gly Phe Gly Pro Asn Pro
 65              70                  75                  80

Glu Ser Val Phe Ala Ile Pro Asp Val Val Arg Gly Leu Lys Leu Ala
                 85                  90                  95

Ile Glu His Phe Thr Lys Pro Gly Ser Ala Ile Ile Val Pro Leu Pro
                100                 105                 110

Ala Tyr Pro Pro Phe Ile Glu Leu Pro Lys Val Thr Gly Arg Gln Ala
            115                 120                 125

Ile Tyr Ile Asp Ala His Glu Tyr Asp Leu Lys Glu Ile Glu Lys Ala
130                 135                 140

Phe Ala Asp Gly Ala Gly Ser Leu Leu Phe Cys Asn Pro His Asn Pro
145                 150                 155                 160

Leu Gly Thr Val Phe Ser Glu Glu Tyr Ile Arg Glu Leu Thr Asp Ile
                165                 170                 175

Ala Ala Lys Tyr Asp Ala Arg Ile Ile Ala Asp Glu Ile His Ala Pro
            180                 185                 190

Leu Val Tyr Glu Gly Thr His Val Val Ala Ala Gly Val Ser Glu Asn
            195                 200                 205

Ala Ala Asn Thr Cys Ile Thr Ile Thr Ala Thr Ser Lys Ala Trp Asn
210                 215                 220

Thr Ala Gly Leu Lys Cys Ala Gln Ile Phe Phe Ser Gly Glu Ala Asp
225                 230                 235                 240

Val Lys Ala Trp Lys Asn Leu Ser Asp Ile Thr Arg Asp Gly Val Ser
                245                 250                 255

Ile Leu Gly Leu Ile Ala Ala Glu Thr Val Tyr Asn Glu Gly Glu Glu
                260                 265                 270

Phe Leu Asp Glu Ser Ile Gln Ile Leu Lys Asp Asn Arg Asp Phe Ala
            275                 280                 285

Ala Ala Glu Leu Glu Lys Leu Gly Val Lys Val Tyr Ala Pro Asp Ser
290                 295                 300

Thr Tyr Leu Met Trp Leu Asp Phe Ala Gly Thr Lys Ile Glu Glu Ala
305                 310                 315                 320

Pro Ser Lys Ile Leu Arg Glu Glu Gly Lys Val Met Leu Asn Asp Gly
                325                 330                 335

Ala Ala Phe Gly Gly Phe Thr Thr Cys Ala Arg Leu Asn Phe Ala Cys
            340                 345                 350

Ser Arg Glu Thr Leu Glu Glu Gly Cys Ala Val Ser Pro Ala Cys Cys
            355                 360                 365

Lys
```